United States Patent [19]

Klawitter et al.

[11] Patent Number: 4,535,483
[45] Date of Patent: Aug. 20, 1985

[54] SUTURE RINGS FOR HEART VALVES

[75] Inventors: Jerome J. Klawitter, Austin, Tex.; Harry W. Cromie, Pittsburgh, Pa.

[73] Assignee: Hemex, Inc., Austin, Tex.

[21] Appl. No.: 458,618

[22] Filed: Jan. 17, 1983

[51] Int. Cl.³ ............................................. A61F 1/22
[52] U.S. Cl. .................................... 623/2; 128/334 R
[58] Field of Search .................. 3/1.5, 1; 128/334 R, 128/334 C

[56] References Cited

U.S. PATENT DOCUMENTS

| | | | |
|---|---|---|---|
| 3,491,376 | 1/1970 | Shiley | 3/1.5 |
| 3,691,567 | 9/1972 | Cromie | 3/1.5 |
| 3,725,961 | 4/1973 | Magovern et al. | 3/1.5 |
| 3,763,548 | 10/1973 | Anderson | 29/445 |
| 4,197,593 | 4/1980 | Kaster et al. | 3/1.5 |
| 4,254,508 | 3/1981 | Bokros | 3/1.5 |
| 4,308,624 | 1/1982 | Klawitter | 3/1.5 |

FOREIGN PATENT DOCUMENTS 1180087  10/1964  Fed. Rep. of Germany ........... 3/1.5

Primary Examiner—Ronald L. Frinks
Attorney, Agent, or Firm—Fitch, Even, Tabin & Flannery

[57] ABSTRACT

Suture rings are provided for heart valves having surrounding stiffening protrusions that are either integral parts of the heart valve bodies or are rigid rings held in interference fit within peripheral grooves of heart valve bodies. Metal retainer rings engage the stiffening protrusions to lock the retainer rings to the valve bodies and carry fabric coverings on their exterior surfaces that are suturable to the heart tissues. Deformable portions of the retainer rings are used to provide engagement between the retainer rings and the protrusions and also to permanently position bands that secure the fabric coverings to the retainer rings.

20 Claims, 10 Drawing Figures

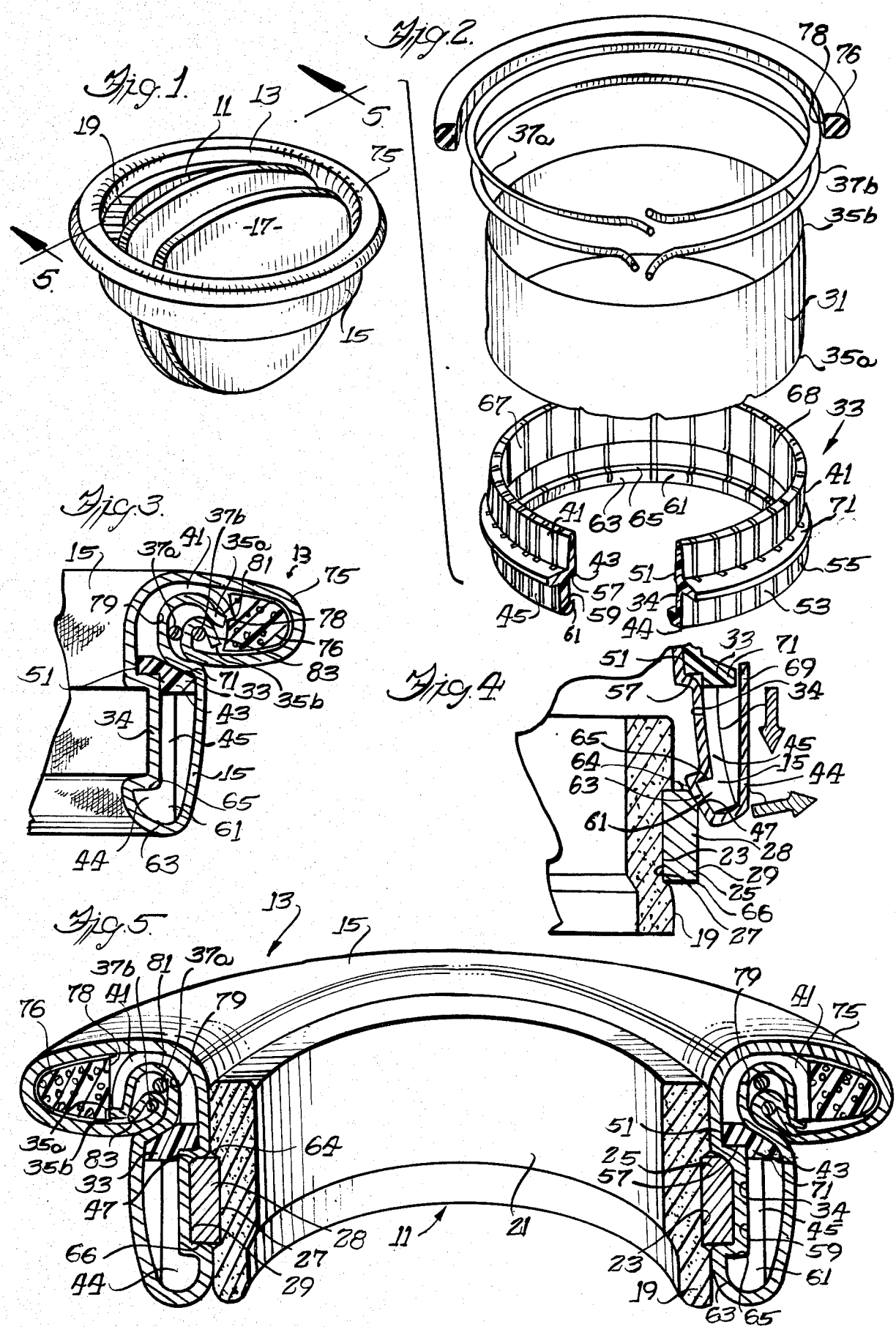

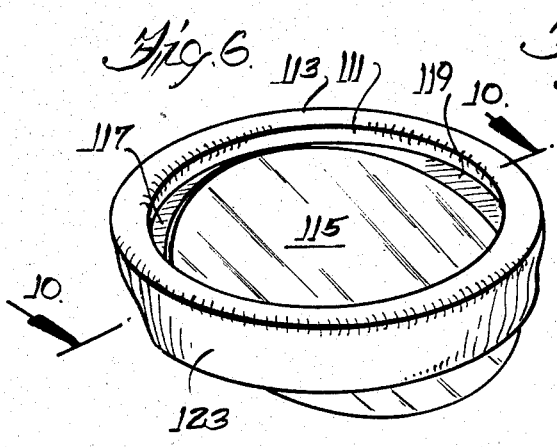
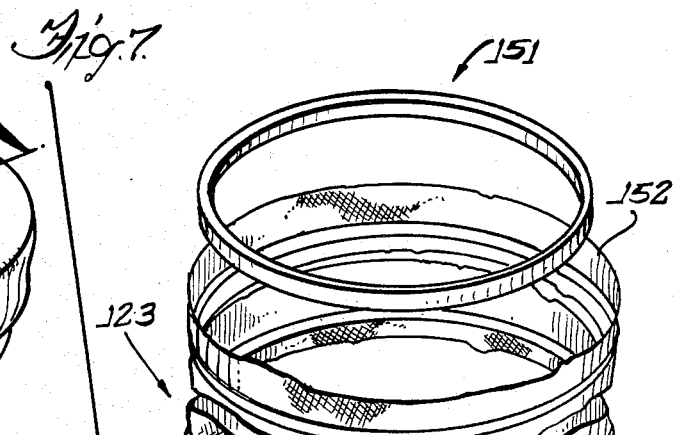
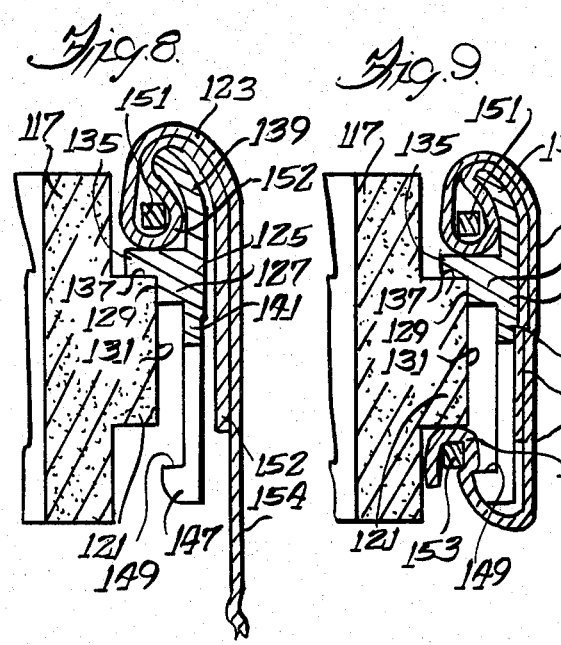
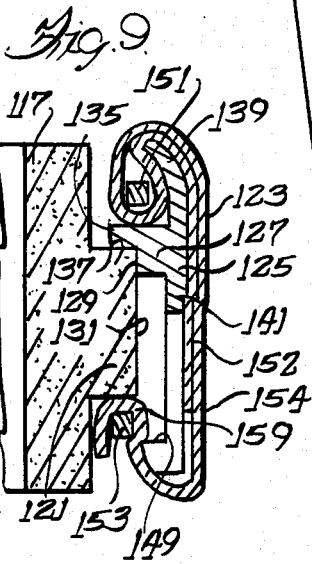
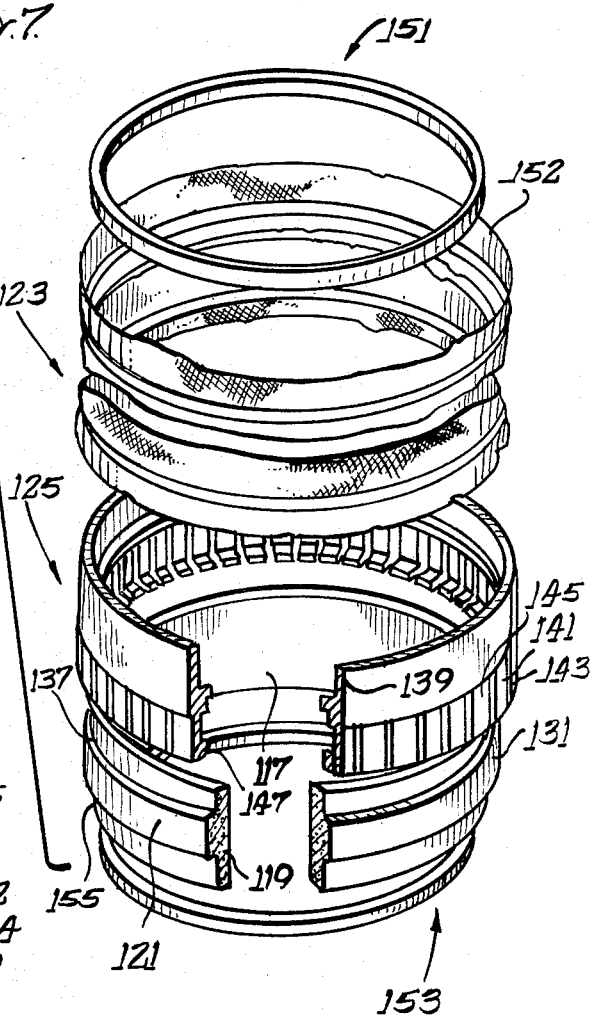
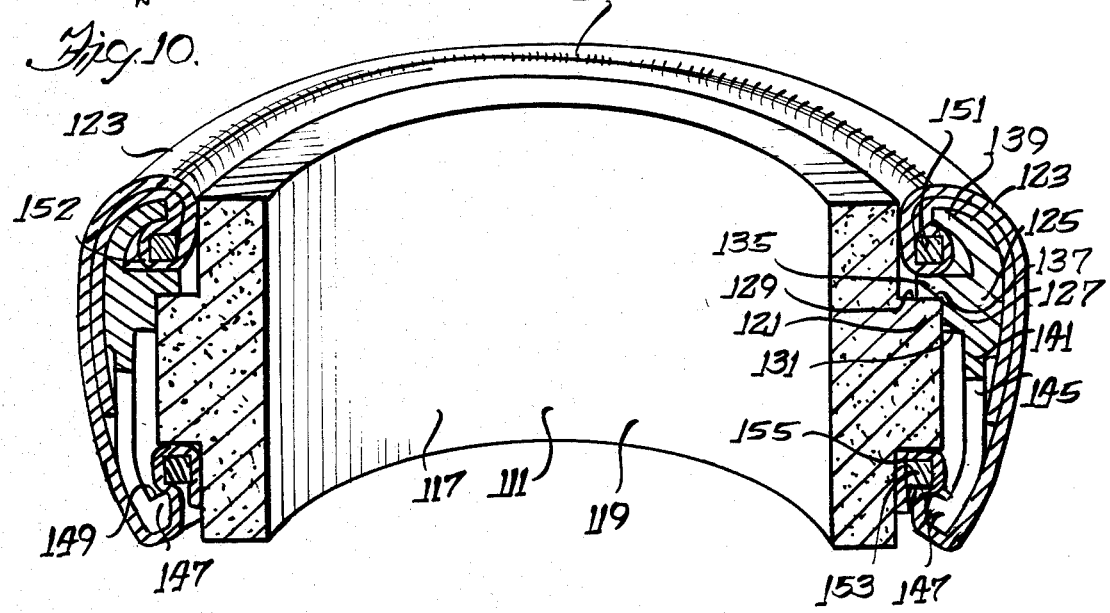

SUTURE RINGS FOR HEART VALVES

The present invention relates to heart valve prostheses and more particularly to improved suture rings for implanting heart valves.

BACKGROUND OF THE INVENTION

Artificial heart valves for surgical implantation in the human heart are check valves which permit blood flow through the valves in a downstream direction but block regurgitation of blood in a reverse or upstream direction. In spite of the relatively simple concept of a check valve, much effort has been exerted in improving the design of heart valves which are implanted into the human heart and should desirably function reliably for a lifetime.

Heart valves having pivoting valve members, either in the form of a single occluder, such as described in U.S. Pat. No. 4,123,805, or a pair of leaflets, such as described in U.S. Pat. No. 4,254,508, provide good flow characteristics and quick response to blood flow. As a means for inserting heart valves into the heart, they commonly have attached fabric members suturable to the tissues of the heart. Frequently the fabric member is attached to a separate suture ring which is applied to the periphery of the heart valve body or orifice ring, for example, as described in U.S. Pat. No. 3,763,548. An important design consideration for heart valves and their suture rings is minimizing their thickness in a radial direction in order to maximize the size of the blood flow passageway of the heart valve that is inserted in a natural passageway of a given size. Newer, thinner heart valve bodies formed, for example, as unitary structures of pyrolytic carbon have enabled larger valve passageways to be provided; however, thin heart valve bodies sometimes lack the rigidity that is desirable for such valves.

In some cases, deformability of the heart valve body is advantageous as where the occluder and valve body have cooperating depressions and protrusions and the resiliently deformable valve body is deformed to permit insertion of the occluder and the resilient valve body is allowed to spring back into engagement with the occluder. In other instances, engagement of the occluder with the valve body may be accomplished by deformation of the occluder or by other means. In any case, deformability of the valve body is undesirable in an assembled heart valve. Although after insertion into the heart, the valve is not subjected to substantial deforming forces, the possibility remains that a surgeon could inadvertently deform the orifice ring and dislocate the occluder as he is inserting the valve into the heart. The heart valve body in combination with the suture ring should therefore provide sufficient resistance to deformation that there is no danger of displacing the occluder during insertion into the heart.

The need continues for improved suture rings which together with the heart valve bodies occupy a narrow region along the heart passageway and which together provide the rigidity needed to assure that the valve body will not be deformed during insertion. The fabric member portion of the suture ring should be continuous, fully covering any exposed metal portions of a suture ring, and exposed seams and fabric ends are to be avoided.

SUMMARY OF THE INVENTION

Suture rings, having fabric coverings for suturing to the heart tissues, are provided that lock onto protrusions which surround orifice rings of heart valves adding stiffness thereto. The suture rings have inner surfaces which overlie outer surfaces of the protrusion, first end portions which engage one end surface of the protrusion and second end portions which are deformable to engage the opposite end surfaces of the protrusions. The fabric coverings are secured to the retainer rings with bands, and deformable sections of the retainer ring permanently position the bands in place along the retainer ring.

In a preferred embodiment, the protrusion on which the retainer ring is locked is an outwardly extending portion of a stiffener ring received in interference fit in a peripheral groove of the orifice ring.

BRIEF DESCRIPTION OF THE DRAWINGS

FIG. 1 is a perspective view of a bileaflet heart valve and a suture ring assembly, embodying various features of the invention, for insertion in a mitral location;

FIG. 2 is an exploded perspective view of the suture ring assembly;

FIG. 3 is an enlarged cross-sectional view of the suture ring of FIG. 2 in a condition nearly ready for mating with the heart valve;

FIG. 4 is an enlarged fragmentary cross-sectional view similar to FIG. 3 illustrating mating of the assembly with the heart valve;

FIG. 5 is an enlarged cross-sectional view taken generally along line 5—5 of FIG. 1;

FIG. 6 is a perspective view of a heart valve having a single disc occluder and an alternative embodiment of a suture ring assembly, embodying various features of the invention, for insertion in an aortic location;

FIG. 7 is an exploded perspective view of the suture ring assembly and heart valve body of FIG. 6;

FIG. 8 is an enlarged cross-sectional view of the suture ring of FIG. 6 preparatory to mating with the heart valve body;

FIG. 9 is an enlarged fragmentary cross-sectional view, similar to FIG. 8, showing the valve body slipped into the prepared suture ring of FIG. 8; and FIG. 10 is an enlarged cross-sectional view taken along line 10—10 of FIG. 6.

DETAILED DESCRIPTION OF THE PREFERRED EMBOIDMENT

Illustrated in FIG. 1 is a heart valve 11 which carries a suture ring assembly 13 particularly adapted for insertion in a mitral location. The suture ring assembly has an outer covering 15 of porous fabric which can be sutured to the tissue of the heart and to which the fibrous tissues of the heart will attach during healing.

The illustrated heart valve 11 has two leaflets or valve members, such as described in the above-mentioned '508 Patent in which a pair of generally semi-circular leaflets 17 are mounted within an orifice ring or valve body 19 for pivoting between an open position to allow blood flow through the orifice or passageway and a closed position to block blood flow. The leaflets 17 are mounted in the orifice ring by suitable interengagement means (not shown) which may include depressions and/or protuberances on the interior of the orifice ring and cooperating depressions and/or protuberances at the periphery of each leaflet, which interengagement means forms no part of the present invention.

Such orifice rings are often formed of materials that are somewhat resiliently deformable in order to be deformed for insertion of the valve members 17. When the orifice ring 19 returns to its annular configuration, the depressions and/or protrusions of the orifice ring and valve members 17 mount the valve members for pivotal motion. A particularly suitable material for formation of valve members and orifice rings is pyrocarbon, such as that sold under the name PYROLITE, which has a surface with highly thromboresistant characteristics. Orifice rings formed of pyrocarbon or of materials such as graphite coated with pyrocarbon may be deformed sufficiently for mounting of the valve members.

Heart valves 11 generally have orifice rings 19 with shallow outwardly facing annular grooves 23. In accordance with one aspect of the present invention, the suture ring assembly 13 includes an inner stiffener ring 25, which interfits with the annular groove and stiffens the orifice ring against deformation during surgical implantation, an outer surrounding retainer ring 33 and a fabric member 31 which is suturable to the tissues of the heart. An inner surface 27 of the stiffener ring 25 is held in interference fit within the shallow annular groove 23, and the thickness of the ring is such that its outer surface 29 extends radially outward of the outer surface of the orifice ring. The retainer ring 33 has an interior region or groove 34 which accommodates the outwardly protruding portion 28 of the stiffener ring 25 with a fabric member 31 interposed and held therebetween.

The fabric member 31, which is initially tubular in shape, is wrapped into a closed loop configuration around the retainer ring 33 with its ends 35a, 35b joined together to form the cover 15 which fully surrounds the retainer ring, and the junction between the overlapping ends 35 of the tubular fabric member is locked into a non-exposed position. Enclosure of the junction is achieved by a deformable section comprised of a ring of tines 41 that extend from a rigid annulus 43 of the retainer ring and are crimped into a curved configuration around the junction.

Generally, the application of the suture ring assembly 13 to the heart valve is as follows. The stiffener ring 25, which is formed of metal, is shrink-fitted into an interference fit within the outwardly facing groove 23 by first heating it to expand its diameter. The fabric member 31 is wrapped into its closed loop configuration around the retainer ring 33 and its ends are joined with a pair of cords or ties, one tie 37a banded around a first end 35a and a second tie 37b banded around the second end 35b. The ring of tines 41, which have been partially deformed or pre-crimped outward to a first position (as shown in FIG. 3), are further deformed or crimped toward the annulus 43 to a second permanent position to lock in the ties and surrounding fabric. The fabric covered retainer ring 33, is thereafter snapped onto the stiffener ring 25 by means of a deformable segment consisting of a ring of resilient prongs or tangs 45 that extend from the annulus 43 in the opposite direction from the tines 41.

So that the invention may be more fully understood, the suture ring assembly will now be described in greater detail. Although it is understood that the heart valve and suture ring assembly will be oriented within the heart valve in the orientation of the replaced natural heart valve, for ease of explanation, the vertical orientation of the several members will be described with reference to FIGS. 1-5 of the drawings.

The stiffener ring 25 is of annular shape having a generally rectangular cross section; however, the upper outer edge 47 is chamfered to facilitate application of the retainer ring 33 as described hereinbelow. The inner surface 27 of the stiffener ring is generally matched to the shape of the shallow groove 23 of the orifice ring 19 with the inside diameter of the stiffener ring substantially equal to the root diameter of the groove and the height of the stiffener ring substantially equal to that of the groove. The thickness of the stiffener ring is greater than the depth of the groove so that the outer surface 28 of the ring protrudes radially outward of the orifice ring 19.

As a means of fitting the stiffener ring 25 over one end of the orifice ring 19 and into the groove 23, the stiffener ring is first heated to high temperatures until it expands sufficiently to slide over the ring. The heat-expanded stiffener ring is positioned around the groove and cooled to ambient temperatures whereat it seats snugly in the groove. The metal of which the stiffener ring is formed has a coefficient of thermal expansion sufficient to permit its application, when heated, to the orifice ring. Although the stiffener ring in the final assembly is shielded by the fabric covering 15 from contact with blood or tissue, the metal used to form the stiffener ring is selected for biocompatibility and thromboresistance. A Co-Cr alloy is a preferred material for formation of the stiffener ring which may be heated to about 900° F. for application to the orifice ring.

The retainer ring 33 is fabricated as a unitary, generally tubular piece of metal appropriately slit to provide the rings of tines 41 and tangs 45 extending in opposite directions from the central annulus 43. Although the retainer ring is fully covered with fabric in the complete heart valve-stiffener ring-retainer ring assembly, the metal is also selected for biocompatibility and thromboresistance. The central portion of the metal retainer ring has a thickness sufficient that it will not deform under the conditions of suture ring assembly. The tangs 45 are less thick and in the process of suture ring assembly will deflect, but the "memory" of the resilient metal returns the tangs to their original configuration. The tines 41 are relatively thin and are deformed past their elastic limit and during suture ring assembly assume the shape into which they are deformed. A preferred metal for fabrication of the retainer ring is titanium. Other metals, such as stainless steel, may also be used to fabricate the retainer ring, or a material having similar deformable properties might be used instead of metal.

The central annulus 43 is relatively thick giving shape and rigidity to the retainer ring 33. The inner surface 51 of the annulus has a diameter slightly greater than the outer diameter of the orifice ring to accommodate a layer of fabric therebetween.

Below the central annulus 43, the inwardly facing annular groove or region 34 is formed to accommodate the outwardly protruding portion 28 of the stiffener ring 25 leaving a lower annular rim 44. The groove 34 is proportioned to accommodate a single layer of the tubular fabric member 31 interposed between the stiffener ring and the retainer ring along an upper surface or overhang 57, a vertical surface 59 and a lower surface 65 of the groove.

To facilitate interconnection of the retainer ring and the orifice ring-stiffener ring assembly, the retainer ring 33 is divided by a plurality of slits 55 into the ring of resilient tangs 45 extending downward from the central annulus 43. The lower rim 44 is divided by the slits 55 into radially inwardly extending lugs 61 at the ends of the tangs 45. Preferably, the undersurfaces 63 of the lugs 61 are rounded to facilitate camming of the lugs over the upper surface 64 and the outer surface 29 of the stiffener ring 25 during mating of the retainer ring to the orifice ring-stiffener ring assembly. Between the lugs 61 and the annulus, the thickness of the tangs 45 is such to allow them to deform outwardly during retainer ring application and snap back thereafter to surround and engage the stiffener ring.

Above the annulus 43, a thin tubular portion 67 of the retainer ring 33 is divided by a plurality of slits 68 into the ring of tines 41. The thin tines are deformed past their elestic limit upon the application of sufficient crimping force thereto. The tines 41 are precrimped prior to application of the fabric member, using suitable dies, into the outwardly curved configuration seen in FIG. 3, and the precrimped tines, along with an outwardly extending flange 71 of the annulus 43, provide an outwardly facing annular region 79.

The fabric member 31 is formed of fabric selected for lifetime durability as well as compatibility with blood and heart tissue. A woven or knitted fabric provides porosity for ingrowth of heart tissue, and a preferred material for the fabric member is Dacron knit fabric. The length of the tubular fabric member is sufficient to fully surround the retainer ring closely following its contours as well as providing a radially extending flap 75 for suturing to the heart tissue.

To facilitate handling and suturing, it is preferred that the flap 75 be thickened, and this is preferably accomplished by means of a resilient polymeric filler ring 76, e.g., formed of low density or foam polytetrafluoroethylene, such as that sold under the trademark Teflon. The filler ring has a semi-elliptical cross section, its inner surface 78 being substantially vertical and having a diameter matched to the outside diameter of the finally crimped tines 41 as seen in FIG. 5. The Teflon filler ring 76 is easily penetrated by suturing needles. Alternatively, the flap could be thickened using a longer fabric member 31 and folding and layering its ends, but the close knit of the fabric makes it difficult for suturing needles to penetrate multiple layers.

The tubular fabric member 31 is wrapped around the retainer ring 33 prior to its application to the orifice ring 19 and fitted stiffener ring 25. The fabric member 31 is shown in FIG. 2 in its simple tubular configuration; however, prior to application to the retainer ring, the fabric member is preferably pre-creased, e.g., by steam pressing, in order to closely conform to the shape of the retainer ring which it is to cover. Various dies are used in pre-creasing the fabric member to conform to the contours of the retainer ring. The fabric is creased to follow the contours of inwardly facing annular region 79. On the outside of the retainer ring, a segment of the fabric stretches from the undersurface 60 of the lugs to the upper surface of the central portion of the retainer ring 33.

Within the outwardly facing annular region 79 provided by the precrimped tines 41, the first or lower end 35a of the fabric member is securely tied with one of the suture cords 37a leaving a short length 81 of the first end extending beyond the point of tying. The outwardly curved tines prevent upward displacement of the tightly tied cord. The filler ring 76 is then placed around the ring of precrimped tynes 41, its inner surface 78 being deformed by the tines which have not yet been fully crimped, as seen in FIG. 3. The second or upper end of the fabric member 31 is brought around the filler ring 76, tucked below the tines 41 and tied tightly with the second cord 37b within the annular region 79. The second end overlaps the first end completing the closed loop configuration of the fabric covering 15. The free terminus 83 of the second end extending beyond the tie is folded back upon itself into the region radially exterior of the two ties so it lies along the free length 81 of the first end leaving no exposed fabric ends to fray or interfere with the flow of blood. In order that the second cord may be knotted, its ends may be threaded through the fabric and tied exterior of the closed fabric loop. The cords maintain the fabric in position along the retainer ring and filler ring 76. The tines 41 are then crimped to their final configuration so they extend substantially back to the flange 71 of the annulus 43, locking the cords 37 and fabric end portions in the annular region 79 between the crimped tines and the flange.

The loose multilayered flap 75 of the fabric member is steam-pressed for the final time into a flat annular configuration extending radially outward of the upper end of the retainer ring for suturing to the heart tissues and in particular to the tissue at the interior of a passageway remaining after excision of a natural mitral valve. The fabric-covered suture ring at this stage may be coated with vapor-deposited carbon, such as that sold under the name Biolite, giving the exposed fabric a highly thromboresistant surface.

The covered, coated retainer ring is ready for application to the heart valve-stiffener ring assembly. The retainer ring is pressed downward over the orifice ring-stiffener ring assembly as seen in FIG. 4. When the lower curved surfaces 63 of the tang lugs 61 contact the chamfered upper edge 47 of the stiffener ring, the tangs 45 resiliently deform outwardly, and when the flat upper surfaces 65 of the lugs reach the bottom edge of the stiffener ring, the tangs spring back inward locking the retainer ring in surrounding relationship about the stiffener ring. With the horizontal upper surface 57 of the groove 34 located along the horizontal upper surface 67 of the stiffener ring 25 and the horizontal lower surface 65 of the groove located along the horizontal lower surface 66 of the stiffener ring, the retainer ring is securely locked to the stiffener ring.

With the inwardly facing annular region 34 of the retainer ring thus engaged about the outer surface 28 of the stiffener ring, the retainer ring is secured to the orifice ring with the fabric member interposed and firmly held between the retainer ring and the stiffened orifice ring. During application of the retainer ring to the orifice ring-stiffener ring assembly, any slack in the inner portion of the fabric member is taken up so the fabric, which surrounds the retainer ring, now fully covers the surfaces of the protruding portion of the stiffener ring.

Illustrated in FIG. 6 is an alternative embodiment of a heart valve 111 and a surrounding a suture ring 113 particularly adapted for insertion in an aortic location. Although the heart valve 111 and suture ring 113 will in use be orientated in accordance with anatomy of the heart, for ease of description, the heart valve and suture ring are described as having an upper and a lower end, with reference to FIGS. 6-10. The illustrated heart valve 111 has a single disc occluder 115 mounted within an orifice ring or valve body 117 for pivoting between an open position to allow blood flow through a central passageway 119 and a closed position to block blood flow through the passageway. In the illustrated heart valve 111, the valve body 117 is stiffened by being formed with an integral encircling protrusion 121. Because of the stiffness provided by the integral protrusion, it may be desirable to form to be the occluder 115 sufficiently resiliently deformable to permit its insertion into the valve body 117, or the occluder and/or mounting means may be fabricated to permit mounting of the occluder in a substantially non-deformable valve body. It is to be understood that the aortic suture ring 113 is equally suitable for use with a heart valve such as that illustrated with reference to FIGS. 1-5, having a stiffener ring in interference fit in a peripheral groove of the heart valve body.

Physiological differences between the mitral and aortic locations require some design differences between suture rings used in mitral locations and suture rings in aortic locations. The mitral valves extend between two heart chambers, and when a defective natural mitral valve is removed, a broad surface is provided along the entrance to the opening. Thus, a broad suture flange, such as that in the embodiment of FIGS. 1-5, is preferably attached thereto. In the aortic location, however, the suture ring must be sutured to the walls of the passageway, and such a broad suturing flange is not appropriate for an aortic valve suturing ring. Furthermore, although a fabric tube 123 in the aortic ring fully covers the surfaces of a retainer ring 125, the fabric tube 123 is preferably not interposed between the valve body protrusion 121 and the retainer ring in order to further minimize the thickness of the valve body-suture ring assembly, but rather, the fabric tube is secured between the valve body 117 and retainer ring 125 at locations both above and below protrusion 121.

The retainer ring 125 is fabricated as a unitary, generally tubular piece of metal. The main body is a narrow central annulus 127 having an interior surface 129 proportioned to fit closely about the outer surface 131 of the encircling protrusion 121 and an annular flange 135, that extends inward of the annulus 127 and lies adjacent the upper surface 137 of the protrusion 121. A thin tubular section 139 extends a substantial distance upward from the body and is deformed inward in the assembled unit. Because it is not intended to greatly deform this section, there should be no need to provide slots to accommodate deformation without buckling, and in the illustrated embodiment, none are provided.

A lower thin tubular section or portion 141 extends a substantial distance downward from the main body, and because this tubular section is deformed substantially during its application to the valve body, a plurality of slots 143 (FIG. 7) are formed extending upward into this lower tubular section creating a plurality of individually deformable tangs 145. The lower end of the tubular portion 141 is formed with a rib that extends inward to provide each tang with an inward protuberance 147. Although the tangs 145 in the aortic suture ring resemble the tangs in the herein before-described mitral suture ring, each having an inward protuberance, the tangs of the aortic suture ring are crimped into engagement about the valve body protrusion 121, rather than being snap-fit onto the protrusion, as is the case in the mitral valve suture ring. Thus, the protuberances 147 do not extend sufficiently inward to lie below the protrusion until they are irreversably deformed by crimping. The narrow, horizontal upper surfaces 149 of the tang protuberances 147 provide secure locking when the tangs are crimped to lock the retainer ring 125 to the valve body. The interior surface 129 of the main body does not extend the full distance along the valve body protrusion 121 permitting the tangs 145 to be formed of greater length and therefor more easily crimped.

Although the fabric tube 123 is not intended to fully encircle the retainer ring 125 and is not interposed between the interior surface of the annulus and the outer surface of the protrusion, the length of the fabric tube is preferably substantially longer than the height of the retainer ring to provide a double layer of material along the exterior of the retainer ring to be sutured to the heart tissues and to also provide portions that envelop the upper and lower ends and are tucked between the retainer ring and the valve body and held therein by means of dam rings or bands 151, 153. The fabric tube is preferably precreased for fitting around the ends of the retainer ring and looping around upper and lower fabric-holding bands 151, 153.

The fabric-holding bands 151,153 secure the ends of the fabric tube to the retainer ring to fully cover those portions of the retainer ring that would otherwise remain exposed after the retainer ring is locked to the valve body, and they are formed of rigid metal. Rigid metal bands are preferable to tied cords for securing fabric ends between two generally rigid members, i.e., the valve body 117 and the retainer ring 125, and facilitate assembly.

The illustrated bands 151, 153 have rectangular cross sections being cut from cylindrical tubes; however, bands having round cross sections or other configurations could be used. The bands typically have cross-sectional dimensions of about 0.7 mm in the axial direction by 0.5 mm in the radial direction for a rigid metal, such as titanium.

The upper band 151 is proportioned for insertion between the upper tubular segment 139 of the retainer ring 125 and the heart valve body 117 above the protrusion 121 leaving sufficient clearance around the band for a looped portion of the fabric tube 123 to surround the ring. The outside diameter of the upper ring is closely matched to the interior diameter of the upper tubular segment 139 whereby the fabric is captured between the band 151 and the tubular segment, and a slight amount of inward crimping of the upper tubular segment is sufficient to retain the upper band 151 in its installed position on the retainer ring. Insertion of the fabric-surrounded upper band 151 and inward crimping of the upper tubular segment 139 is generally completed before the retainer ring is applied to the valve body, the upper tubular segment serving no function in locking the retainer ring 125 to the valve body.

The lower band 153 is proportioned to be received between the tangs 145 and the valve body 117 as shown in FIG. 9, where it can be seen that the outside diameter of the lower band 153 is significantly less than the uncrimped interior diameter of the ring of tangs 145. In locking the retainer ring 125 to the valve body, the tangs are crimped a substantial distance inward serving the dual functions of pinning the lower end of the fabric tube between the band 153 and the lower surface 155 of the protrusion 121 and holding the lower band 153 in permanent position between the retainer ring and the protrusion to lock the retainer ring to the valve body.

To assemble the suture ring 113, the retainer ring 125 is placed on a jig (not shown), and the fabric tube 123 is extended through the central passageway of the retainer ring with that portion of the fabric tube which is to serve as an inner fabric layer 152 at the upper end. The upper band 151 is then inserted into retainer ring along the inside of the upper tubular segment 139 and inside of the fabric tube 123 and pushed downward to hold the fabric tube against the inwardly extending flange 135. Thereupon, a die is used to crimp the upper tubular segment 139 radially inward until its upper edge overhangs the upper band 151, locking the upper band in place and firmly pinning the fabric tube between the upper band and the upper tubular segment 139 and flange 135. With the fabric tube pinned in place, the upper portion 152 of the fabric tube 123 above the ring is folded over the upper edge of the upper tubular segment 139 and downward along the outside of the retainer ring, extending almost to its lower end. Next, the remaining portion 154 of the fabric tube 123 is pulled up through the central passageway of the retainer ring and likewise folded over the top and along the outside of the retainer ring overlying the inner layer 152 of the fabric tube. At this stage, the partially prepared suture ring 20 (FIG. 8) is ready for application to a heart valve body 117 having a surrounding protrusion 121, and the retainer ring 125 is removed from the jig.

The valve body 117 and partially prepared retainer ring 125 are then mated (as shown in FIG. 8). The retainer ring 125 is inverted and inserted into another jig (not shown). The valve body 117 is inserted into the retainer ring 125 so that the body protrusion 121 seats on the suture ring flange 135 with the outer surface of the protrusion 131 fitting closely along the interior surface 129 of the central annulus 127. That portion of the fabric tube 123 that extends below the tangs is folded inward, and the lower band 153 is pushed downward into the annular region between the inverted valve body 117 and the tangs 143 until it seats against the protrusion 121, carrying the surrounding fabric inward so that a loop 159 of fabric is pinned between the band and the valve body 117. Finally, the tangs 145 are crimped inward to lock the suture ring to the valve body by pressing them against the lower band 153 and the fabric tube loop 159 to force them against protrusion. Any excess fabric tube that extends outward beyond the end of the valve body and retainer ring is trimmed away. The fabric may also be coated with vapor-deposited carbon.

Several advantages of the heart valves should now be more fully appreciated. The suture rings are fully assembled with the heart valves prior to their insertion into a heart where they are implanted by suturing. The protrusions, whether they are integral with the valve bodies or are separate stiffener rings, provide rigidity to otherwise thin, somewhat flexible, valve bodies eliminating the possibility that the valve members may be released from the valve bodies during surgical implantation into the heart. The outer fabric coverings have no exposed seams, through which blood might seep or which might be pulled loose, nor any exposed ends. The simple assembly of the retainer rings and the convenient means for locking the retainer rings onto the valve bodies substantially reduce the assembly time, which represents a significant portion of present heart valve manufacturing costs.

The invention has been described in terms of certain preferred embodiments; however, modifications obvious to one with ordinary skill in the art may be made without departing from the scope of the invention.

Various features of the invention are set forth in the following claims.

What is claimed is:

1. A suture ring for a heart valve having a valve body providing a blood flow passageway, occluder means mounted within said valve body for opening and closing the passageway and a protrusion around the valve body having first and second end surfaces, the suture ring comprising a retainer ring having an interior surface proportioned to surround said protrusion, inwardly extending means for engaging said first end surface of the protrusion and a deformable end portion for engaging the second end surface to lock said retainer ring onto the protrusion, a fabric tube surrounding said retainer ring, said fabric tube being interposed between said retainer ring and said protrusion, band means for securing the opposite ends of said fabric tube together, and deformable means which forms a part of said retainer ring for holding said band means in permanent position, said deformable means being deformed from a first position adjacent said band means to a second permanent lock positon about said band means.

2. A suture ring for a heart valve having a valve body providing a blood flow passageway, occluder means mounted within said valve body for opening and closing the passageway and a protrusion around the valve body having first and second end surfaces, the suture ring comprising a retainer ring having an interior surface proportioned to surround said protrusion, inwardly extending means for engaging said first end surface of the protrusion and a deformable end portion for engaging the second end surface to lock said retainer ring onto the protrusion, a fabric tube, band means for securing the ends of said fabric tube to said retainer ring so that exposed surfaces of said retainer ring when it is locked onto said protrusion are fully covered by said fabric tube, said band means comprising a first band for securing one end of said fabric tube to said retainer ring and a second band for securing the other end of said fabric tube to said retianer ring, and deformable means which forms a part of said retainer ring for holding at least said first band in permanent position.

3. A suture ring according to claim 2 wherein said deformable means comprises a first deformable retainer ring section for permanently positioning said first band and a second deformable retainer ring section for permanently positioning said second band.

4. A suture ring according to claim 2 wherein said deformable end portion provides means for permanently positioning one of said bands.

5. A suture ring according to claim 4 wherein said deformable end portion holds said one band in permanent position between the retainer ring and the valve body.

6. A suture ring according to claim 5 wherein said deformable end portion is permanently crimped to permanently position said one band.

7. A suture ring according to claim 2 wherein said first and second bands are rigid rings.

8. A suture ring according to claim 2 wherein said second end portion of said retainer ring is resiliently deformable so that said retainer ring may be snap-fit about said protrusion, said second end portion deforming outwardly as it is forced over said protrusion and thereafter returning inwardly to engage said second end surface of the protrusion.

9. A suture ring according to claim 2 wherein said fabric tube surrounds said retainer ring, said fabric tube being interposed between said retainer ring and said protrusion with said band means holding opposite ends of said fabric tube together.

10. A suture ring in accordance with claim 9 wherein said retainer ring has tine means substantially encircling said band means.

11. A suture ring in accordance with claim 10 wherein said retainer ring has an outwardly extending flange, and said tine means are crimped to extend substantially to said flange.

12. A suture ring according to claim 2 wherein said deformable end portion of said retainer ring comprises a ring of deformable tangs.

13. In combination,
a heart valve comprising
a valve body providing a blood flow passageway,
occluder means mounted within said valve body for opening and closing said passageway, and
an annular groove around the valve body;
a stiffener ring in interference fit within said groove,
a portion of said stiffener ring extending outward of said groove to provide a protruding portion having first and second end surfaces; and
a suture ring comprising
a retainer ring having an interior surface proportioned to fit about said protruding portion of said stiffener ring, radially inwardly extending means for engaging said first end surface and a deformable end portion for engaging said second end surface to lock said retaining ring onto said stiffener ring, and
a fabric member covering exposed surfaces of said retainer ring.

14. A combination according to claim 13 wherein said fabric member is tubular and band means secure opposite ends of said tubular fabric member to said retainer ring.

15. A combination according to claim 14 wherein said retainer ring has a deformable section for holding said band means in association with said retainer ring.

16. A suture ring for a heart valve having a valve body providing a blood flow passageway, occluder means mounted within said valve body for opening and closing the passageway and a protrusion around the valve body having first and second end surfaces, the suture ring comprising
a retainer ring having an interior surface proportioned to surround said protrusion, inwardly extending means for engaging said first end surface of the protrusion and a deformable end portion for engaging the second end surface to lock said retainer ring onto the protrusion,
a fabric tube surrounding said retainer ring, said fabric tube being interposed between said retainer ring and said protrusion,
band means for securing opposite ends of said fabric tube together with said fabric tube fully covering surfaces of said retainer ring,
said retainer ring having deformable tine means and an outwardly extending flange, and said tine means being crimped to extend substantially to said flange to substantially encircle said band means.

17. A suture ring in accordance with claim 1 wherein said deformable means are a ring of tines substantially encircling said band means.

18. A suture ring in accordance with claim 17 wherein said retainer ring has an outwardly extending flange, and said tines are crimped to extend substantially to said flange.

19. A suture ring according to claim 1 wherein said second end portion of said retainer ring is resiliently deformable so that said retainer ring may be shap-fit about said protrusion, said second end portion deforming outwardly as it is forced over said protrusion and thereafter returning inwardly to engage said second end surface of the protrusion.

20. A suture ring according to claim 1 wherein said deformable end portion of said retainer ring comprises a ring of deformable tangs.

* * * * *

UNITED STATES PATENT AND TRADEMARK OFFICE
CERTIFICATE OF CORRECTION

PATENT NO. : 4,535,483

DATED : August 20, 1985

INVENTOR(S) : Jerome F. Klawitter and Harry W. Cromie

It is certified that error appears in the above-identified patent and that said Letters Patent is hereby corrected as shown below:

Column 5, line 16, correct the spelling of --elastic--.

Column 5, line 57, change "79" to --34--.

Column 5, line 58, change "60" to --63--.

Column 7, line 6, change "to be the occluder 115" to

--the occluder 115 to be--.

Column 9, line 41, after "against" insert --the--.

Column 10, line 45, correct the spelling of --retainer--.

Column 12, line 35, correct the spelling of --snap-fit--.

Signed and Sealed this

Eleventh Day of February 1986

[SEAL]

Attest:

DONALD J. QUIGG

Attesting Officer

Commissioner of Patents and Trademarks